United States Patent [19]

Carome et al.

[11] Patent Number: 5,396,325
[45] Date of Patent: Mar. 7, 1995

[54] OPTICAL SENSOR

[75] Inventors: Edward F. Carome, Cleveland; Michael D. Rainer, Chagrin Falls, both of Ohio

[73] Assignee: The Mercury Iron & Steel Co., Cleveland, Ohio

[21] Appl. No.: 20,615

[22] Filed: Feb. 22, 1993

[51] Int. Cl.$^6$ .............................................. G01N 2/41
[52] U.S. Cl. .................................. 356/128; 356/133; 356/136
[58] Field of Search ...................... 356/128, 133, 136

[56] References Cited

U.S. PATENT DOCUMENTS

| | | | |
|---|---|---|---|
| 2,780,131 | 11/1952 | Lanneau et al. | 88/14 |
| 3,520,619 | 7/1970 | Ward | 356/133 |
| 3,540,025 | 11/1970 | Levin et al. | 340/234 |
| 4,274,705 | 6/1981 | Miller | 350/96.15 |
| 4,422,714 | 12/1983 | Benoit et al. | 350/96.15 |
| 4,440,022 | 4/1984 | Masom | 73/293 |
| 4,676,638 | 6/1987 | Yasuda | 356/237 |
| 4,699,511 | 10/1987 | Seaver | 356/136 |
| 4,749,274 | 6/1988 | Aoki et al. | 356/136 |
| 4,770,129 | 9/1988 | Miyata et al. | 356/133 |
| 4,803,470 | 2/1989 | Fineman | 340/583 |
| 4,895,444 | 6/1990 | Miyata et al. | 356/128 |
| 4,962,746 | 10/1990 | Miyata et al. | 123/613 |
| 4,998,022 | 5/1991 | Tregay | 250/577 |
| 5,083,018 | 1/1992 | Rhyne | 356/133 |
| 5,229,833 | 7/1993 | Stewart | 356/128 |
| 5,255,075 | 10/1993 | Cush | 356/128 |

Primary Examiner—Robert P. Limanek
Assistant Examiner—David Ostrowski
Attorney, Agent, or Firm—Watts, Hoffmann, Fisher & Heinke Co.

[57] ABSTRACT

According to the present invention, there is provided an optical sensor capable of detecting, identifying or measuring a property of a solid, liquid or gas which is in contact with its measuring surface. The preferred sensor comprises an optically transparent sensing element with at least one surface, an optical energy source, means for conducting optical energy from the source to the sensing element at a specific, precisely determined angle and a photodetector. The measuring surface of the sensing element forms an interface with the substance to be measured. Optical energy is partially reflected from the interface formed at the planar surface of the transparent element toward the photodetector. It has been discovered that the resulting signal from the photodetector is proportional to the refractive index of the medium covering the outer surface of the transparent element.

29 Claims, 4 Drawing Sheets

OPTICAL SENSOR

FIELD OF THE INVENTION

This invention relates generally to the field of optical sensors, and more specifically to an optical sensor which measures local reflected intensity of optical energy directed by a first light guide toward a boundary surface between the sensor and a medium under test.

BACKGROUND OF THE INVENTION

Numerous types of optical sensors sensitive to changes in refractive index have been characterized in the art. These include devices which operate by measuring optical energy internally reflected at an interface with a surrounding medium. Optical fibers may serve to direct light onto the interface and may also serve as the optical detectors themselves. Despite the availability of such sensors, there remains a need in the art for a rugged sensor using fiber-optics which is easy and inexpensive to produce, immune from electromagnetic interference and intrinsically safe in explosive environments.

DISCLOSURE OF THE INVENTION

According to the present invention, there is provided an optical sensor capable of detecting, identifying or measuring a property of a solid, liquid or gas which is in contact with its measuring surface. The sensor may be configured as a hand-held instrument, a probe-type instrument for in-situ measurement, a laboratory instrument or as an in-line instrument for continuous measurement or process control. The preferred device includes a temperature sensor and/or a thermoelectric device, or both, to compensate for temperature sensitivity in the sensor.

The preferred sensor comprises an optically transparent sensing element with at least one surface, first and second light guides, an optical energy source and a photodetector. The measuring surface of the transparent element forms an interface with the substance to be measured. One end of each light guide is fixed to the transparent element. The opposite end of the first light guide is coupled to the optical energy source, while the opposite end of the second light guide is fixed to the photodetector.

The first light guide conducts optical energy from the optical energy source into the transparent element, the light guide being fixed at a specific, precisely determined angle. This optical energy is partially reflected from the interface formed at the planar surface of the transparent element. Reflected optical energy is collected by the second light guide in the same plane as the first light guide and conducted to the photodetector. It has been discovered that the resulting signal from the photodetector is proportional to the refractive index of the medium covering the outer surface of the transparent element.

Whenever optical energy is incident on a polished boundary between two media with different refractive indices some of the incident optical energy is reflected and some is refracted (transmitted) into the second medium. Optical energy is reflected at an angle equal to the angle of incidence. At a boundary surface of two materials with different refractive indices the intensity of the reflected optical energy is dependent on the ratio of the refractive indices of the two materials, the polarization of the incident optical energy, and the angle of incidence. The amount of reflected optical energy is greater when the difference between the refractive indices of the two materials is greatest.

In the case of optical energy incident from an optically denser medium (i.e., a medium with a relatively higher index of refraction) to an optically rarer medium (i.e., a medium with a relatively lower index of refraction), there is a certain "critical angle" of incidence, relative to the normal, or perpendicular the interface beyond which all optical energy is totally internally reflected. For all optical energy incident at an angle greater than the critical angle total internal reflection occurs. In the sensor of the present invention, optical energy is preferably incident upon the boundary surface at less than the critical angle so no total internal reflection occurs within the measuring range of the sensor.

Optical energy incident at an angle to a surface less than the critical angle is governed by the Fresnel reflectance equation:

$$R = 1/2 \left( \frac{\sin^2 (\theta_i - \theta_r)}{\sin^2 (\theta_i + \theta_r)} + \frac{\tan^2 (\theta_i - \theta_r)}{\tan^2 (\theta_i + \theta_r)} \right), \quad (1)$$

where "$\theta_i$" is the angle of incidence of the optical energy and "$\theta_r$" is the angle of the refracted optical energy. At a specific angle of incidence, if the refractive index of the covering medium approaches the refractive index of the glass layer, the percent of reflectance decreases and more optical energy passes into the covering medium. Since the change in the reflected optical energy is dependent on changes in the angle of incidence and the refractive index of the covering medium, the above equation may be used as the basis of a detection scheme.

Applications of the preferred sensor include detecting changes in refractive index of a thin porous coating of metal or other porous substance coating the measuring surface; detecting the presence and/or concentration of specific chemicals, compounds, substances, polymers, toxins, pathogens, antibodies, antigens or biomolecules; selectively measuring changes in refractive index at the measuring surface as a result of adsorption, desorption, chemisorption, binding, chemical and/or physical reaction, or electro-chromic effect; and detecting the dew point at a specific temperature or the freeze point of various liquids.

Therefore, it is an object of the invention to provide an optical sensor for detecting changes in the index of refraction of a substance forming an interface with a transparent element. These and other objects, features and advantages of the invention will become clearer from the following description of the preferred embodiment read in connection with the accompanying drawings.

DETAILED DESCRIPTION OF THE PREFERRED EMBODIMENT

Figure 1:
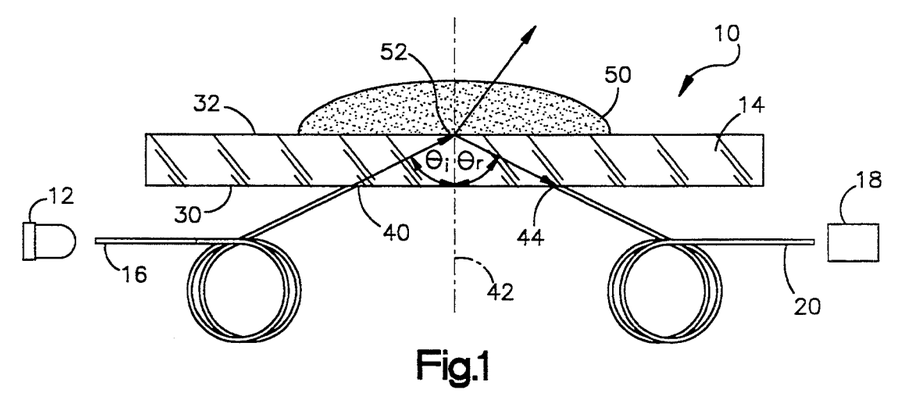
FIG. 1 is a diagram of an optical sensor embodying the invention.

As best shown in FIG. 1, a first embodiment of the present invention is an optical sensor 10 including a light-emitting diode ["LED"] optical energy source 12 coupled to an element 14 by means of a first large-diameter-core multimode optical fiber 16 and a photodetector 18 coupled to the element 14 by means of a second large-diameter-core multimode optical fiber 20. The element 14 is in the form of a thin glass plate having a planar light-incident surface 30 parallel to a planar measuring surface 32. The optical fiber 16 is fixed to the light-incident surface 30 at the position 40 so that optical energy transmitted from the optical energy source 12 through the fiber 16 is directed through the element 14 at an oblique angle to the measuring surface 32. The optical fiber 20 is fixed to the light-incident surface 30 of the element 14 at position 44 in the same plane as the optical fibre 16 to receive a sample of optical energy transmitted through the element 14 away from the measuring surface 32.

The term "optical energy" is used to emphasize that the preferred optical sensor 10 is not limited to optical energy sources 12 which produce optical energy within the visible spectrum. While the preferred sensor 10 is shown with a LED serving as an optical energy source 12, other optical energy sources useful with the invention include lasers, laser diodes, incandescent bulbs, fluorescent bulbs, halogen bulbs or a combination of such sources. For particular applications, it may be preferable that the optical energy produced by the optical energy source be "monochromatic" in the sense that it is limited to one wavelength or a narrow bandwidth. The optical energy source may be modulated for particular applications. Reflectors, lenses or other optical components (not shown) may be added to alter the path fo the optical energy between the fibers 16, 20 or the element 14.

Optical energy from the optical energy source 12 is directed into the element 14 by the optical fiber 16 at a specified angle $\theta_i$ relative to the normal 42 to the measuring surface 32. While the preferred means shown for light conduction is an optical fiber, other means such as a light pipe, a light guide or a gradient index lens may be used. As shown in FIG. 1, the optical fiber 16 is fixed near its end 40 at an angle $\theta_i$ with a normal 42 to the light receiving surface 30 by means of an adhesive (not shown). Preferably, the refractive index of the adhesive is suitably matched to the indices of refraction of the element 14 and the optical fiber 16 to minimize distortion of the optical energy transmitted by the optical fiber 16.

The photodetector 18 receives and measures the intensity of optical energy reflected at the surface 32 or otherwise transmitted through the element 14 away from the measuring surface 32. Preferred photodetectors 18 include photodiodes and phototransistors, but may also include other types of detectors such as photomultipliers, charge coupled devices or a linear array of photodiodes. While the photodetector 18 is shown in FIG. 1 as coupled to the element 14 by means of the optical fiber 20, the photodetector 18 may also be secured directly to the element 14 with a suitable adhesive. Needless to say, the photodetector 18 should be sensitive to those wavelengths of optical energy reflected or otherwise transmitted through the element 14 away from the measuring surface 32 which form the basis for the optical sensing function.

In the embodiment shown in FIG. 1, the element 14 and the photodetector 18 are coupled by means of an optical fiber 20. While the preferred means shown for coupling the element 14 and the photodetector 18 is an optical fiber, other means such as a light pipe, a light guide or a gradient index lens may be used. An end 44 of the optical fiber 20 is positioned along the light-incident surface 30 of the element 14 so as to maximize the receipt of optical energy reflected at the measuring surface 32. To further maximize the receipt of reflected optical energy, the end 44 of the optical fiber 20 is oriented at an angle equal to $\theta_r$ relative to the normal 42 of the light-incident surface 30 of the element 14. As with the optical fiber 16, the optical fiber 20 is oriented near its end 44 at an angle such that the surface at the end 44 lies flat along the light-incident surface 30 when the central axis of the optical fiber 20 near the end 44 makes an angle equal to $\theta_i$ with a normal to the light receiving surface 30. The end 44 of the optical fiber 20 is fixed to the light-incident surface 30 by means of an adhesive (not shown) having an index of refraction suitably matched to minimize optical energy loss between the element 14 and the optical fiber 20.

One application of optical sensor 10 is for determining indices of refraction. When used as a refractometer, the measuring surface 32 is brought into contact with a substance 50. Optical energy from optical energy source 12 travels through the optical fiber 16. The optical energy exits the optical fiber 16 into the element 14 and is incident on the measuring surface 32 in the area of a sensing region 52. Optical energy incident on the sensing region 52 is partially transmitted into the substance 50 at its interface with the measuring surface 32 and is partially reflected back through the element 14 away from the measuring surface 32 towards the light-incident surface 30 and the optical fiber 20. Optical energy reflected at the sensing region 52 is conducted by the optical fiber 20 to the photodetector 18, the intensity of optical energy reflected onto photodetector 18 being a function of the refractive index of the substance 50 in contact with sensing region 52.

Because the refractive indices of many substances such as aqueous solutions are very temperature dependent, a thermistor 60 (FIG. 2) is required for temperature compensation. The thermistor or other thermal sensor is preferably located on or near the light-incident surface 30 of the element 14 to provide an accurate measure of the temperature of the substance 50.

Figure 2:
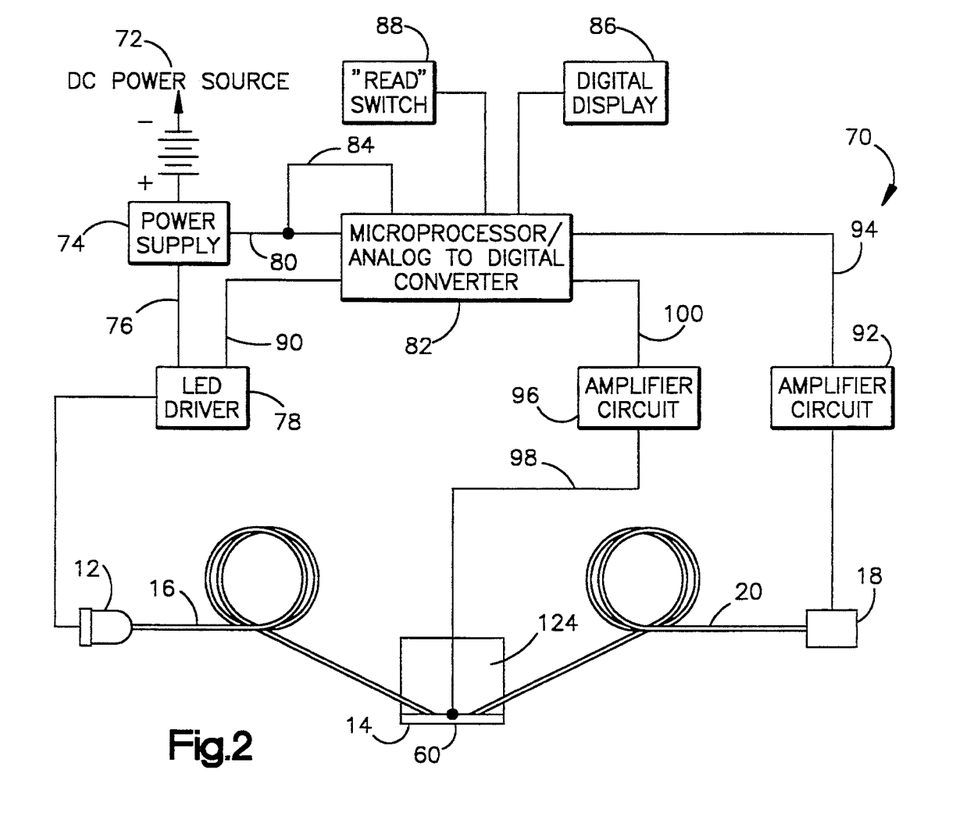
FIG. 2 is a schematic diagram of an electronic circuit for use in connection with the optical sensor or FIG. 1.

Electronic circuitry 70 for driving the optical sensor 10 as a refractometer is shown schematically in FIG. 2. A DC power source 72 (preferably a battery) provides power to a power supply 74. One analog power line 76 connects the power supply 74 with an LED driver 78, while another analog power line 80 connects the power supply 74 with a microprocessor 82. The voltage output by the power supply 74 is monitored by the microprocessor 82 on a line 84.

The microprocessor 82 communicates with the LED driver 78, the thermistor 60, photodetector 18, a digital display 86 and a "READ" switch 88. Line 90 connects the microprocessor 82 with the LED driver 78, which in turn is connected to the optical energy source (in the preferred mode, LED) 12. Amplifier circuit 92 receives the output from the photodetector 18 and relays the amplified output to the microprocessor 82 on the line 94. Similarly, amplifier circuit 96 receives the output from the thermistor 60 on the line 98 and relays the amplified output to the microprocessor 82 on the line 100. The lines 94 and 100 communicate with the microprocessor 82 through an analog-to-digital converter (not shown) which may be either internal or external to the microprocessor.

The LED driver 78 includes an amplifier supply and a current regulating circuit for supplying an adjustable supply current to the optical energy source 12. The preferred "READ" switch 88 is a push button switch of either the normally open or normally closed type depending on the signal characteristics of the microprocessor 82.

When a user presses the "READ" switch 88 the microprocessor 82 signals the LED driver 78 to pulse the optical energy source 12 through the line 90. The photodetector 18 generates a signal corresponding to the intensity of optical energy reflected at the measuring surface 32 which is amplified by the amplifier 92 and sent to the microprocessor 82 via the line 94. Additionally, the microprocessor 82 monitors the signal of the thermistor 60 which is amplified by the amplifier 96 and carried to the microprocessor by the line 100. The signals from the photodetector 18 and the thermistor 60 are digitized and the microprocessor 82 compensates for the temperature indicated by the thermistor 60. The microprocessor then displays a result corresponding to the desired units of measurement on the digital display 86. When the "READ" switch 88 is released, the microprocessor 82 resets the LED driver 78 to repeat the process of pulsing the optical energy source 12.

Figure 3:
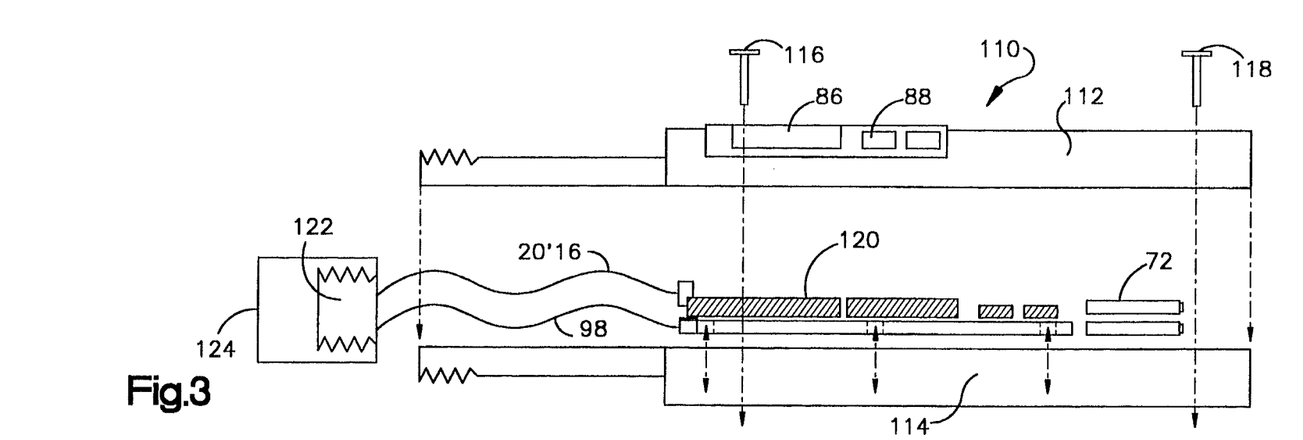
FIG. 3 is a schematic diagram of a probe-type instrument incorporating the optical sensor of FIG. 1.

A handheld probe-type instrument 110 incorporating the optical sensor 10 and the circuit 70 is shown schematically in FIG. 3. The instrument 110 includes a plastic enclosure in two halves 112, 114 held together by retaining screws 116, 118. These two halves 112, 114 sandwich the internal components of the instrument, including the power source 72 and a printed circuit board 120 for carrying the circuit 70. The digital display 86 and the "READ" switch 88 are mounted on the exterior of half 112. The element 14 and thermistor 60 are contained in a sensor housing 122 in such manner that the measuring surface 32 of the element 14 is exposed at a distal end 124 of the sensor housing 122. The element 14 and thermistor 60 are secured to the printed circuit board 120 by fiber optics 12, 16 (only one shown) and electrical line 98. In practice, the distal end 124 of the sensor housing 122 is exposed to a substance to be tested (not shown) and, when the "READ" switch 88 is pressed, the index of refraction of the substance appears on the digital display 86.

Figure 4:
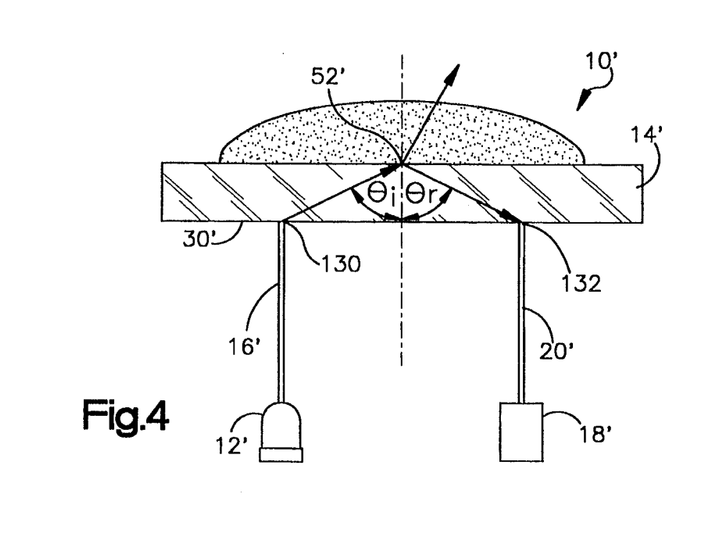
FIG. 4 is a diagram of an alternate optical sensor embodying the invention.
Figure 5:
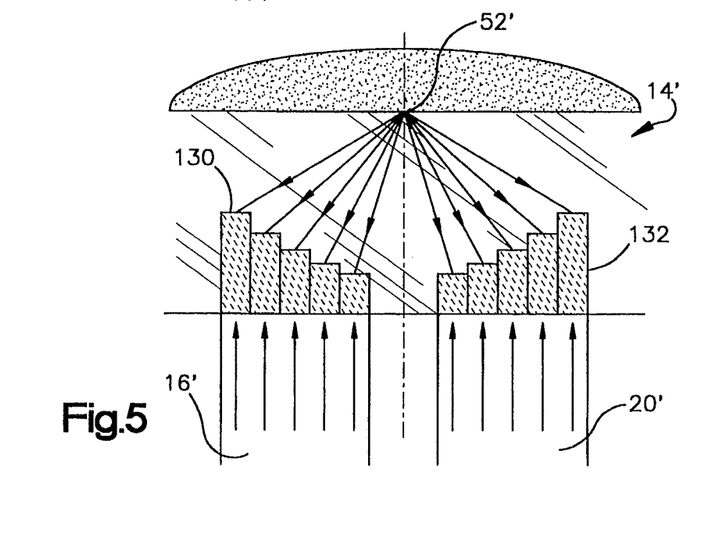
FIG. 5 is a schematic diagram of microdiffraction patterns formed in the element of the sensor of FIG. 4.

FIGS. 4 and 5 show an alternative optical sensor 10'. As in the previous embodiment, the alternative optical sensor includes an optical energy source 12'; optical fibers 16', 20'; an element 14' and a photodetector 18'. In this embodiment the element 14', in the form of a glass plate, has a micro-diffractive pattern 130 (FIG. 4) etched onto its light-incident surface 30' where the fiber 16' is connected to the light-incident surface 30'. This pattern acts as a micro-prism to bend incident optical energy.

Incoming optical energy generated by a light source 12' travels through the optical fiber 16' which is positioned perpendicular to the lower surface 30' of the glass plate directly under the diffraction grating, and held in optical contact with a suitable adhesive (not shown). The micro-diffractive pattern 130 breaks up the wave front of incoming optical energy at each point on the diffraction pattern. The wave front is then reconstituted as a wave traveling in the desired direction to a focal point at the sensing region 52'.

As in the previous embodiment the incident optical energy is reflected at the sensing region 52' at an angle equal to the angle of incidence. This reflected optical energy then passes through another micro-diffraction pattern 132 (FIG. 4) that redirects the optical energy and focuses it into an optical fiber 20', which is perpendicular to the surface of the glass plate. The optical energy is then carried to a photodetector 18' which measures its amplitude.

The micro-diffraction patterns 130, 132 are etched into the glass plate using the same fabrication process used in the micro-electronics industry, a photolithographic process of repeated masking and etching. Diffraction rulings etched to different depths in the glass will cause the secondary wave fronts to be delayed in direct proportion to the depth of the etching. The maximum depth of the etching need only be enough to delay the wave front one full wavelength. Each ruling in the micro-diffraction pattern works to break up the incoming wave front. The optical energy then acts as a set of spherical waves whose constructive and destructive interference create a secondary wave front traveling at an angle to the incoming one. The optical energy is therefore bent by diffraction instead of refraction as in the previous embodiment of this invention.

Figure 6:
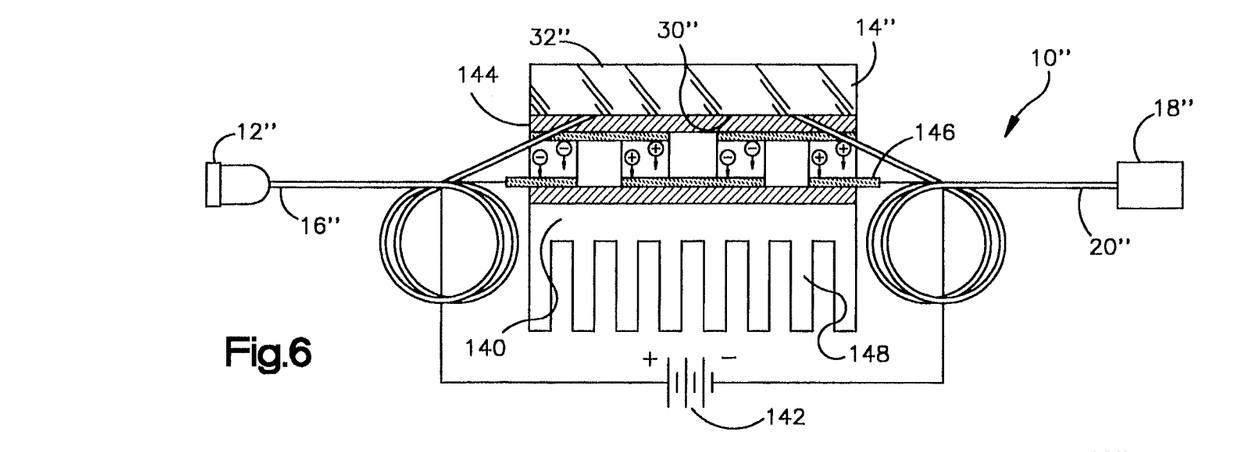
FIG. 6 is a diagram of another alternate embodiment of an optical sensor employing a thermoelectric device for temperature control.

FIG. 6 shows yet another alternative optical sensor 10''. As with the previous embodiments, the alternative optical sensor 10'' includes an optical energy source 12''; optical fibers 16'', 20''; an element 14'' and a photodetector 18''. Because the refractive index of a substance is very closely connected to its temperature, and because refractive index data is frequently published at a specified temperature, it is often desirable to test a given substance at a specific temperature. Circulating water baths are well known in the art for selectively maintaining a substance's temperature while making measurements with optical devices. These water baths are usually large and bulky and often do not respond rapidly. In addition, water baths usually require a considerable power supply and are fitted for use mostly under controlled laboratory conditions.

In this alternative optical sensor 10'' the light-incident surface 30'' of the element 14'' is fitted with a thermoelectric device 140 that selectively keeps the element 14'' at a specified temperature. The preferred thermoelectric device 140 is a semi-conductor based electronic component that acts as a miniature heat pump. When a low DC voltage from a voltage source 142 is applied to the thermoelectric device 140, electrons moving through the semi-conductor material on the cold side 144 absorb heat and transport it to the hot side 146. This heat is then absorbed by a heat sink 148 and transferred to room air.

By changing the polarity of the voltage source 142 the effect is reversed. Since the direction of temperature movement is reversible these devices may be used for precise temperature control as accurate as ±0.1° C. Such thermoelectric devices are known which will cool to −40° C. and heat as high as 100° C.

With this thermoelectric device the measurement temperature could be preset by the electronic control module or by an operator. It would also allow a given sample of liquid to be tested over a rather large range of temperatures to develop a temperature coefficient curve for the solution under test. Response time would be very rapid because of the relative small mass of the sensing element.

Additionally, the thermoelectric device could cool the measuring surface in the presence of air. As the air cooled to its dew point, water droplets would begin to form on the measuring surface 32″ of the sensing element 14″. The formation of water droplets would be detected by a change in the reflectance of this surface. If the operator placed other substances on the measuring surface and cooled them sufficiently, a similar significant change in reflection would be observed at the freezing point of the substance under test.

Figure 7:
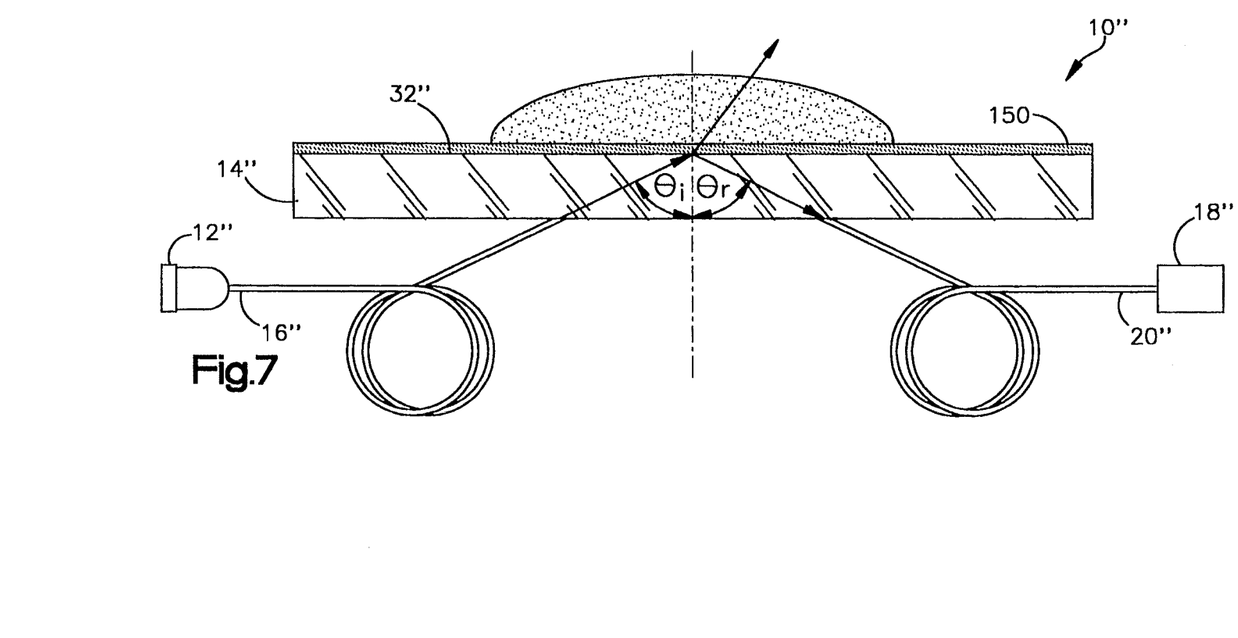
FIG. 7 is a diagram of yet another alternate embodiment of an optical sensor including a coating on the measuring surface of the element.

FIG. 7 shows yet another alternative optical sensor 10′′′. As in the previous embodiments, the alternative optical sensor 10′′′ includes an optical energy source 12′′′; optical fibers 16′′′, 20′′′; an element 14′′′ and a photodetector 18′′′. In this embodiment the measuring surface 32′′′ of the sensing element 14′′′ is coated with a sensing material 150, a thin porous coating of metal or other porous substance which is permeable only by specific chemicals or varies its transmission properties as a function of the refractive index of the covering media. One application of the optical sensor 10′′′ is as a sensor for specific chemicals.

For example, by coating the measuring surface 32′′′ with a 35 $\mu$m thick porous coating of Polytetra-flouro-ethylene (PTFE) it becomes sensitive specifically to oils. With a PTFE coating there would be a noticeable shift in the amount of reflected optical energy in the presence of oils. The invention could therefore be used as an oil leak detector.

In a similar embodiment, measuring surface 32′′′ could be coated with a specific chemical, compound, substance, polymer, or biomolecule. As the substance to be measured binds, adsorbs, desorbs, permeates, dissolves, chemisorbs, reacts physically or chemically with the coating 150 it will produce changes in the refractive index of the coating which can be measured by the optical sensor as previously described.

It is well known that certain chemical species fluoresce under certain wavelengths of light and others chemicals absorb optical energy at specific wavelengths. Still other chemicals exhibit electro-chromic properties by changing color in the presence of specific chemicals. For example, $WO_3$ is an electro-chromic material which changes color as it absorbs hydrogen and forms $H_xWO_3$. By depositing a layer of $Pd/WO_3$ on measuring surface 32′′′ of the optical sensor 10′′′ this change in color can be observed through the light-receiving optical fiber 20′′′.

In another example, by selectively exciting the measuring surface 32′′′ with specific wavelengths of light the fluorescence or absorption of certain chemicals can be observed through the light-receiving optical fiber 20′′′.

Figure 8:
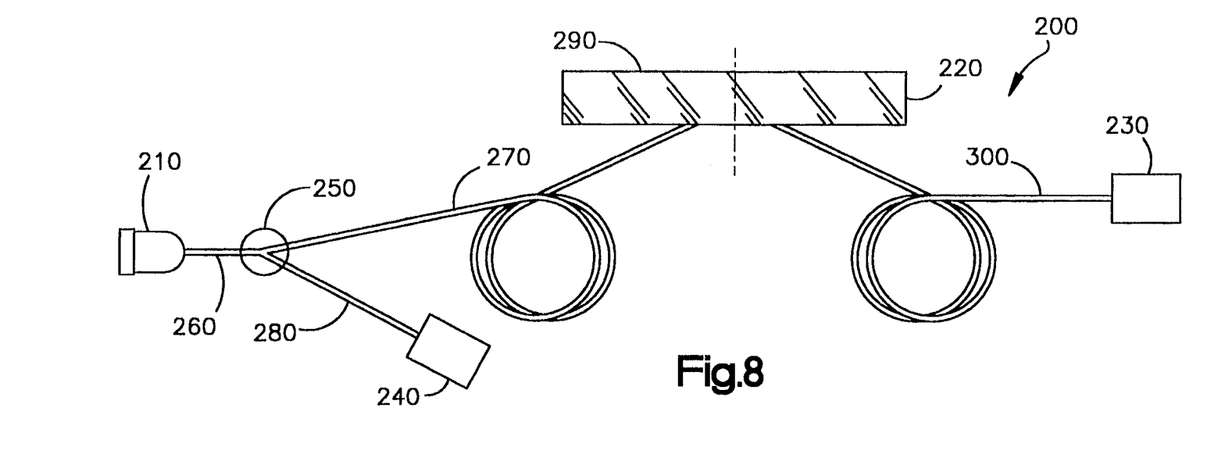
FIG. 8 is a diagram of yet another alternative embodiment of an optical sensor including an optical energy source, a sensor element and two photodetectors.

Though the optical instrument of the present invention has been illustrated with one optical energy source and one photodetector, it is within the scope of the invention to use more than one optical energy source or photodetector. FIG. 8 shows an alternative optical sensor 200 including an optical energy source 210, a sensor element 220 and two photodetectors 230 and 240. Optical energy from the optical energy source 210 is transmitted to a 1×2 fiberoptic splitter 250 by an optical fiber 260. The splitter 250 splits the optical energy into two optical fibers 270 and 280. Optical fiber 270 transmits a portion of the optical energy through the element 220 toward a measuring surface 290. Light transmitted through the element 220 away from the measuring surface 290, as by reflection, is transmitted to the photodetector 230 by an optical fiber 300. On the other hand, light transmitted through the optical fiber 280 bypasses the element 220 and is directed to the photodetector 240.

One advantage of the alternative sensor 200 is that any loss of intensity of the optical energy source 210 may compensated for by comparing the signals generated by the photodetectors 230 and 240. Where the optical energy source 210 is a battery-driven light emitting diode, for example, the intensity of optical energy emitted by the source 210 decreases with time. The absolute intensity of the optical energy reaching the photodetector 230 is dependent on the intensity of optical energy generated by the source 210. Since the optical energy reaching the photodetector 240 bypasses the element 220, its intensity is dependent only on the intensity generated by the source 210. Therefore, the signal generated by the photodetector 240 provides a basis for compensating for decreases in intensity emitted by the optical source 210.

Figure 9:
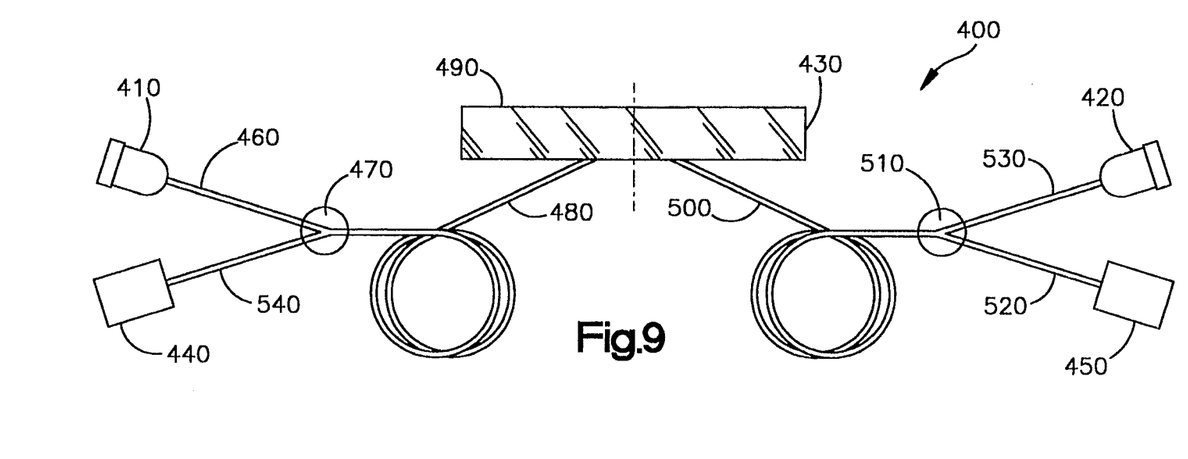
FIG. 9 is a diagram of yet another alternative embodiment of an optical sensor including two optical energy sources, a sensor element and two photodetectors.

Another alternative optical sensor 400 is shown in FIG. 9. The optical sensor 400 includes two optical energy sources 410, 420, an element 430 and two photodetectors 440, 450. Optical energy from the optical energy source 410 is directed through an optical fiber 460 to a 1×2 fiberoptic splitter 470. The optical energy is directed by the splitter 470 through an optical fiber 480 toward a surface 490 of the element. A portion of this optical energy reflected or otherwise transmitted through the element away from the surface 490 is transmitted though an optical fiber 500, a second 1×2 fiberoptic splitter 510 and another optical fiber 520 to the photodetector 450. From the opposite direction, optical energy from the source 420 is conducted through an optical fiber 530, the splitter 510 and the fiber 500 toward the surface 490 of the element 430. A portion of this optical energy which is reflected or otherwise transmitted through the element 430 away from the surface 490 is directed through the optical fiber 480, splitter 470 and optical fiber 540 to the photodetector 440. Providing the two optical energy sources 410, 420 and the two photodetectors 440, 450 along oppositely directed paths enhances the accuracy of the sensor.

Although a preferred embodiment of the invention has been disclosed herein for purposes of illustration, it should be noted that various changes, modifications, and substitutions may be incorporated in such an embodiment without departing from the spirit of the invention, as defined by the claims below.

I claim:

1. An optical sensor comprising:
   an optical energy source for supplying optical energy;

an element including a material transparent to at least a portion of such optical energy defining a planar light incident and a planar measuring surface;

light conducting means connecting the light source and the element for transmitting such optical energy through the element obliquely toward the measuring surface, said light conducting means being optically coupled to said element; and a photodetector communicating with the element in a line of reflection of such optical energy from the measuring surface for measuring a multitude of discrete changes in an intensity of optical energy transmitted through the element away from the measuring surface, and being operative to generate a signal that is a function of the measured changes in said intensity.

2. An optical sensor according to claim 1 wherein the optical energy source is constructed and arranged so that such optical energy is visible light.

3. An optical sensor according to claim 1 wherein the optical energy source is constructed and arranged so that such optical energy is monochromatic.

4. An optical sensor according to claim 1 wherein the optical energy source is modulated.

5. An optical sensor according to claim 1 wherein the optical source includes a component selected from the group comprising a light emitting diode, a laser, a laser diode, an incandescent light, a fluorescent light, a halogen light and ambient light.

6. An optical sensor according to claim 1 wherein the element includes a micro-diffraction pattern etched onto a surface of the element spaced from the measuring surface.

7. An optical sensor according to claim i wherein the sensor includes a lens with an etched micro-diffraction pattern sandwiched between the light conducting means and the element.

8. An optical sensor according to claim 1 wherein the light conducting means includes a microdiffraction pattern etched onto a surface of the light conducting means fixed to the element.

9. An optical sensor according to claim 1 wherein the element contacts a thermoelectric device for controlling the temperature of the optical sensor.

10. An optical sensor according to claim 1 including a coating on the measuring surface.

11. An optical sensor according to claim 10 wherein the coating includes a porous substance which is permeable only by specific chemicals.

12. An optical sensor according to claim 10 wherein the coating interacts physically or chemically with a substance contacting the coating to affect such intensity of optical energy transmitted through the element away from the measuring surface.

13. An optical sensor according to claim 1 wherein the light conducting means includes a component selected from the group comprising an optical fiber, a light pipe, a light guide and a gradient index lens.

14. An optical sensor according to claim 1 wherein the element and the photodetector are connected by connecting means including a component selected from the group comprising an optical fiber, a light pipe, a light guide and a gradient index lens.

15. An optical sensor according to claim 1 wherein the photodetector includes a component selected from the group comprising a photodiode, a phototransistor, a photomultiplier, a charge coupled device, a linear array of photodiodes and an avalanche photodiode.

16. A method for optical sensing of a substance comprising the steps of:

providing an element transparent to selected wavelengths that are interactive with the substance, said element having a planar light incident surface and a planar measuring surface;

directing optical energy including said selected wavelengths through said element from said light incident surface toward said measuring surface using a first light conducting means that is optically coupled to said light incident surface;

contacting the measuring surface with the substance;

measuring an intensity of optical energy transmitted through the element away from the measuring surface using a second light conducting means that is optically coupled to said light incident surface; and determining from such intensity of optical energy a physical property of the substance.

17. A method according to claim 16 wherein the step of determining an optical property of the substance includes determining the absorption of the selected wavelengths.

18. A method according to claim 16 wherein the step of determining a physical property of the substance includes determining an intensity of fluorescence induced by the selected wavelengths.

19. The optical sensor of claim 1 wherein said planar light incident surface and said planar measuring surface are spaced apart.

20. The optical sensor of claim 1 wherein said planar light incident surface and said planar measuring surface are spaced apart and parallel.

21. The optical sensor of claim 1 wherein said light conducting means is in abutting contact with said element.

22. A method of claim 16 wherein said planar light incident surface and said planar measuring surface are spaced apart.

23. A method of claim 16 wherein said planar light incident surface and said planar measuring surface are spaced apart and parallel.

24. An optical sensor comprising:

an optical energy source for supplying optical energy;

an element including a material transparent to at least a portion of such optical energy defining a planar light incident and a planar measuring surface;

light conducting means connecting the light source and the element for transmitting such optical energy through the element obliquely toward the measuring surface, said light conducting means being optically coupled to said element;

a photodetector communicating with the element in a line of reflection of such optical energy from the measuring surface, said photodetector being responsive to a plurality of changes in an intensity of optical energy transmitted through the element away from the measuring surface, and being operative to generate an intensity signal that is related to the intensity of said optical energy reflected from said measuring surface;

a temperature compensator coupled to said element and operative to produce a temperature compensated intensity signal that is a function of a physical property of a substance in contact with said measuring surface.

25. The optical sensor of claim 24 wherein said temperature compensator comprises a thermoelectric device for controlling the temperature of the optical sensor.

26. The optical sensor of claim 24 wherein said temperature compensator comprises a temperature sensor coupled to said element for generating a compensating signal that is coordinated with said intensity signal to produce said temperature compensated intensity signal.

27. The optical sensor of claim 26 wherein said temperature sensor comprises a thermistor.

28. An optical sensor comprising:
an optical energy source for supplying optical energy;
an element including a material transparent to at least a portion of such optical energy defining a planar light incident and a planar measuring surface, said surfaces being spaced apart;
light conducting means connecting the light source and the element for transmitting such optical energy through the element obliquely toward the measuring surface, said light conducting means being in abutting contact with said element;
a photodetector communicating with the element in a line of reflection of such optical energy from the measuring surface, said photodetector being responsive to changes in an intensity of optical energy transmitted through the element away from the measuring surface, and being operative to generate an intensity signal that is proportional to said intensity;
a temperature sensor coupled to said element for generating a compensating signal that is coordinated with said intensity signal to produce a temperature compensated output signal that is a function of a physical property of a substance in contact with said measuring surface.

29. An optical sensor comprising:
an optical energy source for supplying optical energy;
an element including a material transparent to at least a portion of such optical energy defining a planar light incident and a planar measuring surface, said surfaces being spaced apart;
light conducting means connecting the light source and the element for transmitting such optical energy through the element obliquely toward the measuring surface, said light conducting means being optically coupled to said element; and
a photodetector communicating with the element in a line of reflection of such optical energy from the measuring surface, said photodetector being responsive to a plurality of changes in an intensity of optical energy transmitted through the element away from the measuring surface, and being operative to generate a signal that is proportional to said intensity.

* * * * *